US006136753A

United States Patent [19]

Wilson

[11] Patent Number: 6,136,753

[45] Date of Patent: Oct. 24, 2000

[54] METHOD FOR TREATING FUNGUS IN PLANTS

[76] Inventor: Richard Wilson, 1246 W. Hicrest Rd., Glendora, Calif. 91741

[21] Appl. No.: 09/262,570

[22] Filed: Mar. 4, 1999

Related U.S. Application Data

[60] Provisional application No. 60/076,949, Mar. 5, 1998.

[51] Int. Cl.[7] ............................ A01N 55/00; A01N 63/00

[52] U.S. Cl. ............................................ 504/193; 504/118

[58] Field of Search ..................................... 504/193, 118

[56] References Cited

U.S. PATENT DOCUMENTS 5,106,649 4/1992 Spicer et al. ................................ 427/4

5,508,249 4/1996 Narayanan et al. .................... 504/116

*Primary Examiner*—Shelley A. Dodson

*Assistant Examiner*—Alton Pryor

*Attorney, Agent, or Firm*—John E. Wagner; Robert C. Smith; Sam Bernardo

[57] ABSTRACT

A method of reduction and prophylaxis of the sphaerotheca (powdery mildew) in rose plants and other flowering plants. The method involves applying a silicone solution to the surface of a plant. The silicone solution can be a siloxane compound such as a methyl siloxane compound, a polydimethylsiloxane, and cyclic methylated siloxane.

19 Claims, No Drawings

METHOD FOR TREATING FUNGUS IN PLANTS

This application claims the Benefit Date of Provisional Application Ser. No. 60/076,949 filed Mar. 5, 1998.

TECHNICAL FIELD OF THE INVENTION

The invention relates to the field of fungal elimination and, and more particularly to a method of reduction, prophylaxis, and control of the fungi powdery mildew (sphaerotheca) in plants, such as roses by application of silicone solutions.

BACKGROUND OF THE INVENTION

Persons in the agricultural industry expend great efforts and expense in treating crops for infestation with the fungi powdery mildew. In the rose growing industry, powdery mildew (sphaerotheca) harms the quality of the roses harvested.

Presently, there are a variety of products for controlling fungus on plants. The compound fungicidal compound Rubigan®, manufactured by the SePRO Corporation, of 11550 North Meridian Street, Carmel, Ind. 46032, includes the active ingredient fenarimol: alpha-(2-chlorophenyl)-alpha-(4-chlorophenyl) 5-pyrimidinemethanol, and is regarded as one of the most commercially acceptable fungicides available to growers for treatment of roses for powdery mildew. However, as will be discussed below, Rubigan® has limited efficacy in treating rose plants already infected with powdery mildew, and no prophylactic effects. Ortho® [(a Monsanto® company) of San Ramon, Calif.] offers several different products including Ortho RosePride Orthonex® for Insect & Disease Control. Orthonex®, contains Acephate (o,s-dimethyl acetylphosphoramidothiate); triforine (N,N'-[1,4-peperazinediylbis 2,2,2-tricholoroethylidene] bis [formamide]); and hexakis (2-methyl-2-phenylpropyl) distannoxane. Ortho® also sells RosePride Funginex® rose and shrub disease control, with the active ingredient triforine (N,N'-[1,4-peperazinediylbis 2,2,2-tricholoroethylidene] bis [formamide]); and the product Volck Oil spray, which comprises petroleum oil.

Cooke Laboratory Products, of Portland, Oreg., sells three products which are said to have antifungal utility. These are Sulf-R-Spray Dormant Spray Lime-Sulfur Fungicide, which includes Calcium Polysulfide as its active ingredient; Kop-R-Spray, which includes the metallic form of copper from copper ammonium complex; and Cooke® Fungicide, which includes petacholoronitrobenzene as its active ingredient.

Black Leaf Products, of Buckner, N.Y., has a Rose & Ornamental Fungicide with systemic action which includes the active ingredient Dimethyl 4,4'-o-phenylenebis (3-thioallophanate). While the Black Leaf Product is said to be relatively effective, it is quite costly, and so is not widely used.

The following patent references are of interest. U.S. Pat. No. 4,614,675 to Ona et al. disclose an antimicrobic, antistatic siloxane composition and method for treating solid materials, such as fibers and fiber containing materials like fabrics (including natural fibers like hair, wool, silk, flax, and cotton) to control the growth of organisms, including fungi. The composition includes components (A) and (B), with component (A) being used to impart microbial resistance to the solid material, and component (B) being used in combination with component (A) to impart hydrophilicity and antistaticity to the solid materials. Component (A) is a quaternary ammonium salt-containing silane and component (B) is an organopolysiloxane. Ona et al. patent make no mention of use of the composition for application to living organisms, including living plants, or cut flowers. Furthermore, no mention is made of the composition's use in treating powdery mildew (a fungus).

Silicone containing compounds do have known use as antifouling coatings on the hull of boats and the like. For example, U.S. Pat. No. 5,663,215 to Milligan discloses coating compositions containing non-siloxane polymers and a curable organohydrogen polysiloxane or polydiorganosiloxane. These compounds are said to adhere well to items immersed in water to prevent fouling thereof, for example with green and brown algae, barnacles, mussels, and the like. U.S. Pat. No. 5,298,060 to Harakal et al. discloses a method to reduce marine life buildup on a submerged surface by applying to the surface an antifouling coating composition comprised of a combination of silicone fluids and a silicone resin. U.S. Pat. No. 3,702,778 to Mueller discloses that cured silicone rubber helps prevent fouling on the hulls of ships. None of these references mention anti-fungal properties of the compositions or application of the compositions to living organisms, such as roses.

Finally, U.S. Pat. No. 5,466,726 to Inoue et al. discloses an antibacterial, antifungal silicone rubber composition. This reference states that the organopolysiloxane composition can be rendered antibacterial and antifungal by blending in a zeolite containing 0.1 to 15% by weight of a silver ion. Of course, silver has well-known antimicrobial properties.

As a result, in cases of severe powdery mildew infestation, growers sometimes have to resort to destroying the roses, which represent a total loss.

There accordingly remains a need for a low cost method for treating plants for fungi that not only eradicates the fungi, but also provides a prophylaxis against further infection.

BRIEF DESCRIPTION OF THE INVENTION

It is an object of the invention to provide a method to treat plants for fungal infestation. It is a further objective of the invention to control and largely eliminate fungus [such as powdery mildew (sphaerotheca)] from plants by applying a silicone solution (such as polydimethylsiloxanes) to plants, such as shrubbery, and including rose bushes. The fungus will be largely eliminated from the foliage, stems, and flowers.

It is a further aspect of the invention to provide a prophylaxis to help prevent the return of fungus after application with the silicone emulsion.

These objects, and others which will become apparent upon consideration of the following disclosure and appended claims, are obtained by the method of this invention, which briefly stated, comprises applying a silicone emulsion to the surface of a plant. The inventor has found that the application of dilute silicone emulsion provides good utility in eliminating and guarding against the return of powdery mildew in rose bushes.

DESCRIPTION OF THE TABLES

Table 1 is a summary of results for untreated control, silicone solution (18.5% dimethylpolysiloxanes), and with Rubigan®, at 0 days after second application.

Table 2 presents detailed results for untreated control, silicone solution (18.5% dimethylpolysiloxanes), and with Rubigan®, for powdery mildew, leaflet %, at various times after second application.

Table 3 presents detailed results for untreated control, silicone solution (18.5% dimethylpolysiloxanes), and with Rubigan®, for powdery mildew, foliage %, at various times after second application.

Table 4 presents detailed results for untreated control, silicone solution (18.5% dimethylpolysiloxanes), and with Rubigan®, for phytotoxicity effects, (yellowing %) of foliage, at various times after second application.

Table 5 presents detailed results for untreated control, silicone solution (18.5% dimethylpolysiloxanes), and with Rubigan®, for %leaflet drop, at various times after second application.

Table 6 presents detailed results for silicone product, untreated control, and with control (Armor All®) for powdery mildew, foliage % mildew controlled, at various times.

Table 7 presents detailed results for silicone product, untreated control, and with Armor All® for powdery mildew, for phytotoxicity, at various times.

Table 8 presents detailed results for silicone product, untreated control, and with Armor All® for powdery mildew, for leaflet drop, at seven days after second treatment.

DETAILED DESCRIPTION OF THE INVENTION

The present invention comprises a method of controlling fungal infection on plants, and in particular comprises a method of largely eliminating and preventing the return of powdery mildew on roses and other flowering plants.

The inventor has found that the application of silicone solutions, such as polydimethylsiloxanes (available from Dow Corning Corporation, Midland, Mich., and GE Silicones, Waterford, N.Y.,) Armor All® spray (as provided by the Armor All company, of Oakland, Calif., and which also contains polydimethylsiloxanes as its active ingredients) and the like, when applied directly to the surface of the foliage of plants, is effective in removing and acting as a prophylaxis of a large percentage of fungus from the leaves, leaflets, stems, and other parts of the plant. As shown in Tables 1–5, the formulation of the silicone emulsion by GE silicones work quite well in a variety of concentration ranges in controlling powdery mildew in roses. As shown in Tables 6–8, the formulation of Dow Corning products 200, 244 and 346 also function quite well as compared to Armor All® in controlling powdery mildew in roses.

The silicone solution noted in Tables 1–5 is a GE Silicone product, custom formulated by GE Silicone to comprise (18.5% dimethylpolysiloxanes, 2% of an antimicrobial agent, with the balance being water-undiluted state.) Polydimethylsiloxanes are also sometimes referred to as dimethylpolysiloxanes. The GE Silicone silicone solution was custom formulated to have approximately the same composition as the Armor All® product.

The silicone solutions of Tables 6–8 includes the Dow Corning® 200® silicone, the Dow Corning® 244 silicone, and the Dow Corning® 346 silicone emulsion. The Dow Corning® 200® silicone comprises 100% polydimethylsiloxane and has a viscosity of 350 centistokes (dimethylsiloxane is $(CH_3)_3$—Si—O—Si—$(CH_3)_3$ and is polymerized into polydimethylsiloxane chains. Longer chains have greater viscosity.) The Dow Corning® 244 silicone emulsion comprises about 95% of a low viscosity silicone fluid cyclotetrasiloxane (octamethylcyclotetrasiloxane) as its active ingredient, and has the following structure:

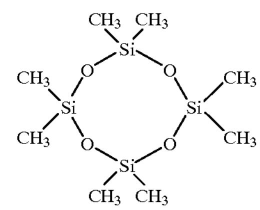

The Dow Corning® 346 silicone emulsion comprises 60% by weight of Dow Corning® 200® polydimethylsiloxane mixed with 40% by weight of water, suspension agents, and antimicrobial agents, and is an easily spreadable emulsion.

As will be discussed in greater detail below, the excellent results in controlling powdery mildew were achieved with all of the silicone solutions utilized. Particularly good results were obtained using two separate treatments with the silicone solutions, and were all substantially better than with the presently used commercial product Rubigan®.

The inventor did observe some incidences of phytotoxicity (yellowing of the foliage) and leaf drop when the GE Silicone silicone emulsions were used, but did not observe these side effects (as compared to untreated roses) when using Armor All® or Dow Corning silicone emulsions. In any case, even with the tested GE silicone formulations, the phytotoxicity and leaf drop would not be significant factors in raising commercial roses under normal commercial growing conditions.

Regardless of the exact formulation of the silicone emulsion used, the silicone emulsion is applied at the desired dilution (in water) and is sprayed directly on the plant upon appearance of the fungus. While one application with the silicone emulsion is effective, the silicone emulsion can be applied a first time, followed by a second application about one week later. Application rates of approximately 50 or 100 gallons of the silicone emulsion in plain water per acre are effective, although lower (20 gallons or less) and higher application rates are also effective. The inventor experimented with the product Armor All® spray directly from the bottle to the plant. The results with Armor All® were extremely good, and additionally, no phytotoxicity in the form of yellowing foliage was observed.

As can be appreciated from the Tables, the silicone emulsions of the invention provides prophylactic effects and prevents the recurrence of fungal infection. For example, with most dilutions of the GE Silicone formulations, e.g. 4.65%, 9.25%, and 18.5% v/v of the dimethylpolysiloxane, the occurrence of fungal infection with powdery mildew after final treatment was substantially lower 14 days after the final treatment than immediately following treatment. Comparing the efficacy of the silicone emulsions with the commercial fungicide Rubigan®, much lower rates of powdery mildew were observed with the silicone emulsions of the invention. The inventor has observed that plants treated with silicone emulsion continue to resist further infection with fungus such as powdery mildew.

Table 1 is a summary of results for untreated control, silicone product (GE Silicone (containing 18.5% of dimethylpolysiloxanes, about 2% of an antimicrobial agent, with the balance being water in the undiluted condition), and Rubigan®, at 0 days after second applications for reduction of powdery mildew on the rose plants' leaflets and foliage. Also shown are phytotoxicity effects of the various solutions and leaf drop effects. As shown, silicone solutions are much more effective in controlling powdery mildew in roses as compared to the standard antifungal agent Rubigan®. Indeed, as shown, below, powdery mildew was reduced from covering about 68% of the leaflets (in the untreated control) to between about 7.5% to 24% in the roses treated with various concentrations of the silicone solution. Rubigan® reduced the powdery mildew only slightly (to about 65% coverage.) With the particular silicone solutions used, some phytotoxicity effects (foliage yellowing) was noted zero days after the second treatment. No leaf drop was observed.

TABLE 1

SUMMARY OF RESULTS FOR UNTREATED CONTROL, SILICONE SOLUTION (18.5% dimethylpolysiloxanes), AND WITH RUBIGAN, AT 0 DAYS AFTER SECOND APPLICATION

| Treatment | Concentration Volume/Volume | Powdery Mildew Leaflet[1], % | Powdery Mildew Foliage[2], % | Phytotoxicity Rose Foliage[3], % yellow | Phytotoxicity Leaflet Drop[4] % |
|---|---|---|---|---|---|
| Untreated Control | N/A | 68.0% | 75.0% | 0.0% | Not observed |
| Silicone Solution (reduced 1:4 silicone solution with water) | 4.625% | 24% | 32.5% | 20.0% | Not observed |
| Silicone Solution (reduced 1:2 silicone solution with water) | 9.25% | 11.0% | 27.5% | 32.5% | Not observed |
| Silicone Solution (undiluted with additional water) | 18.5% | 7.5% | 12.5% | 42.5% | Not observed |
| Rubigan ® [5] | 12 oz/100 gallons | 65.0% | 70.0% | 2.5% | Not observed |

Notes:
[1]Percent mildew per leaflet; five leaflets examined per plot.
[2]Overall percentage of foliage exhibiting mildew symptoms per plot.
[3]Overall percentage of foliage affected per plot. Phytotoxicity is yellowing of leaves.
[4]No leaflet dropping was observed on initial observation.
[5]Rubigan ® applied at its highest suggested concentration.

All plots are sprayed 7 and 14 days before evaluation. Silicone solution was applied at approximately 100 gallons per acre. The above results were after the final treatment. 0%=no powdery mildew, and 100%= completely covered with powdery mildew.

The Silicone Solution comprises dimethylsiloxane 18.5% silicone emulsion, about 2% of an antimicrobial agent, with the balance being water, in the undiluted form.

Turning now to Table 2, this table presents detailed results for untreated control, silicone solution (GE Silicone (containing 18.5% of dimethylpolysiloxanes, about 2% of an antimicrobial agent, with the balance being water in the undiluted condition), and Rubigan®, for powdery mildew, leaflet %, at day 0, day 3, day 7 and day 14 after the second applications for reduction of powdery mildew on the rose plants' leaflets. As is shown, the effectiveness of the various concentrations of the silicone solutions in reducing powdery mildew infection on the leaflets continues to increase from the second application, and ranges to as low as 2% infection (in the full 18.5% strength concentration of dimethylpolysiloxane solution 14 days after the second treatment.) This compares extremely favorably with Rubigan®, which had little effect.

TABLE 2

DETAILED RESULTS FOR UNTREATED CONTROL, SILICONE SOLUTION (18.5% dimethylpolysiloxanes), AND WITH RUBIGAN ® FOR POWDERY MILDEW, LEAFLET %, AT VARIOUS TIMES AFTER SECOND APPLICATION

| Treatment | Concentration Volume/Volume | Powdery Mildew Leaflet[1], day 0 | Powdery Mildew Leaflet[1], day 3 | Powdery Mildew Leaflet[1], day 7 | Powdery Mildew Leaflet[1], day 14 |
|---|---|---|---|---|---|
| Untreated Control | N/A | 68.0% | 59.5% | 63.0% | 57.0% |
| Silicone Solution (reduced 1:4, silicone solution | 4.625% | 24.0% | 9.5% | 10.0% | 6.5% |

TABLE 2-continued

DETAILED RESULTS FOR UNTREATED CONTROL, SILICONE SOLUTION (18.5% dimethylpolysiloxanes), AND WITH RUBIGAN ® FOR POWDERY MILDEW, LEAFLET %, AT VARIOUS TIMES AFTER SECOND APPLICATION

| Treatment | Concentration Volume/Volume | Powdery Mildew Leaflet[1], day 0 | Powdery Mildew Leaflet[1], day 3 | Powdery Mildew Leaflet[1], day 7 | Powdery Mildew Leaflet[1], day 14 |
|---|---|---|---|---|---|
| with water) | | | | | |
| Silicone Solution (reduced 1:2 silicone solution with water) | 9.25% | 11.0% | 4.5% | 0.5% | 0.0% |
| Silicone Solution (undiluted with additional water) | 18.5% | 7.5% | 0.5% | 3.0% | 2.0% |
| Rubigan ® [2] | 12 oz/100 gallons | 65.0% | 70.0% | 58.5% | 59.0% |

Notes:
[1]Percent mildew per leaflet; five leaflets examined per plot.
[2]Rubigan ® applied at its highest suggested concentration.

All plots are sprayed 7 and 14 days before the initial evaluation at approximately 100 gallons per acre. The above results were after the final treatment. 0%=no powdery mildew, and 100%=completely covered with powdery mildew per random leaflet.

The Silicone Solution comprises polydimethylsiloxane 18.5% silicone emulsion, about 2% of an antimicrobial agent, with the balance being water, in the undiluted form.

Referring now to Table 3, this presents detailed results for untreated control, silicone solution (GE Silicone (containing 18.5% of dimethylpolysiloxanes, about 2% of an antimicrobial agent, with the balance being water in the undiluted condition), and Rubigan®, for powdery mildew, foliage %, at day 0, day 3, day 7 and day 14 after the second applications for reduction of powdery mildew on the rose plants' as an overall percentage of foliage exhibiting mildew symptoms per plot. As is shown, the effectiveness of the various concentrations of the silicone solutions in reducing powdery mildew infection on the foliage continues to increase from the second application, and ranges to as low as 5.0% infection (in the half 18.5% strength concentration of dimethylpolysiloxane solution 14 days after the second treatment.) This compares extremely favorably with Rubigan®, which had little effect.

TABLE 3

DETAILED RESULTS FOR UNTREATED CONTROL, SILICONE SOLUTION (18.5% dimethylpolysiloxanes), AND WITH RUBIGAN ®, FOR POWDERY MILDEW, FOLIAGE %, AT VARIOUS TIMES AFTER SECOND APPLICATION

| Treatment | Concentration Volume/Volume | Powdery Mildew Foliage[1], day 0 | Powdery Mildew Foliage[1], day 3 | Powdery Mildew Foliage[1], day 7 | Powdery Mildew Foliage[1], day 14 |
|---|---|---|---|---|---|
| Untreated Control | N/A | 75.0% | 72.5% | 72.5% | 67.5% |
| Silicone Solution (reduced 1:4 silicone solution with water) | 4.625% | 32.5% | 20.0% | 22.5% | 15.0% |
| Silicone Solution (reduced 1:2 silicone solution with water) | 9.25% | 27.5% | 12.5% | 5.0% | 5.0% |
| Silicone Solution (undiluted with additional water) | 18.5% | 12.5% | 7.5% | 7.5% | 7.5% |
| Rubigan ® [2] | 12 oz/100 gallons | 70.0% | 75.0% | 80.0% | 67.5% |

Notes:
[1]Overall percentage of foliage exhibiting mildew symptoms per plot.
[2]Rubigan ® applied at its highest suggested concentration.

All plots are sprayed 7 and 14 days before the initial evaluation at approximately 100 gallons per acre. The above results were after the final treatment. 0%=no powdery mildew, and 100%=completely covered with powdery mildew per random leaflet.

The Silicone Solution comprises polydimethylsiloxane 18.5% silicone emulsion, about 2% of an antimicrobial agent, with the balance being water, in the undiluted form.

Referring now to Table 4, this table presents detailed results for untreated control, silicone solution (GE Silicone (containing 18.5% of dimethylpolysiloxanes, about 2% of an antimicrobial agent, with the balance being water in the undiluted condition), and Rubigan®, at day 0, day 3, day 7 and day 14 after the second applications for %, phytotoxicity effects in the overall foliage. As is shown, there was some yellowing observed in the foliage of roses treated with the silicone solution, ranging as high as 42.5% at the second treatment with the full strength silicone solution, to 12.5% with the half strength dilution at 14 days after the initial solution. Rubigan® did not cause any observable yellowing. The inventor has been able to eliminate phytotoxicity effects by modifying the solution slightly, (see Table 7.)

TABLE 4

DETAILED RESULTS FOR UNTREATED CONTROL, SILICONE SOLUTION (18.5% dimethylpolysiloxanes), AND WITH RUBIGAN ®, FOR PHYTOTOXICITY (YELLOWING %) OF FOLIAGE, AT VARIOUS TIMES AFTER SECOND APPLICATION

| Treatment | Concentration Volume/Volume | Phytotoxicity Rose Foliage[1], % yellow, day 0 | Phytotoxicity Rose Foliage, % yellow, day 3 | Phytotoxicity Rose Foliage, % yellow, day 7 | Phytotoxicity Rose Foliage, % yellow, day 14 |
|---|---|---|---|---|---|
| Untreated Control | N/A | 0.0% | 0.0% | 0.0% | 0.0% |
| Silicone Solution (reduced 1:4 silicone solution with water) | 4.625% | 20.0% | 20.0% | 15.0% | 15.0% |
| Silicone Solution (reduced 1:2 silicone solution with water) | 9.25% | 32.5% | 17.5% | 13.8% | 12.5% |
| Silicone Solution (undiluted with additional water) | 18.5% | 42.5% | 35.0% | 20.0% | 20.0% |
| Rubigan[2] | 12oz/100 gallons | 2.5% | 0.0% | 0.0% | 0.0% |

Notes:
[1]Overall percentage of foliage affected per plot. Phytotoxicity is yellowing of leaves.
[2]Rubigan ® applied at its highest suggested concentration.

All plots are sprayed 7 and 14 days before the initial evaluation at approximately 100 gallons per acre. The above results were taken 7, 10, 14, and 21 days after the final treatment. 0%=no yellowing, and 100%=complete yellowing.

Referring now to Table 5, this table presents detailed results for untreated control, silicone solution (GE Silicone (containing 18.5% of dimethylpolysiloxanes, about 2% of an antimicrobial agent, with the balance being water in the undiluted condition), and Rubigan®, at day 0, day 3, day 7 and day 14 after the second applications for %, leaf drop effects in the overall foliage. As is shown, there was some leaf drop observed in the foliage of roses treated with the silicone solution, ranging as high as 22.5% at the second treatment with the full strength silicone solution at day 14 after the second application. Rubigan® did not cause any observable leaf drop. The inventor has been able to eliminate leaf drop effects by modifying the silicone solution slightly (see Table 8.)

TABLE 5

DETAILED RESULTS FOR UNTREATED CONTROL, SILICONE SOLUTION (18.5% dimethylpolysiloxanes), AND WITH RUBIGAN ®, FOR % LEAFLET DROP, AT VARIOUS TIMES AFTER SECOND APPLICATION

| Treatment | Concentration Volume/Volume | Leaflet drop %, day 0 | Leaflet drop %, day 3 | Leaflet drop %, day 7 | Leaflet drop %, day 14 |
|---|---|---|---|---|---|
| Untreated Control | N/A | not observed | 0.0% | 0.0% | 0.0% |
| Silicone Solution (reduced 1:4 silicone solution with water) | 4.625% | Not observed | 6.3% | 10.0% | 15.0% |
| Silicone Solution (reduced 1:2 silicone solution with water) | 9.25% | Not observed | 10.0% | 15.0% | 16.3% |

TABLE 5-continued

DETAILED RESULTS FOR UNTREATED CONTROL, SILICONE SOLUTION (18.5% dimethylpolysiloxanes), AND WITH RUBIGAN ®, FOR % LEAFLET DROP, AT VARIOUS TIMES AFTER SECOND APPLICATION

| Treatment | Concentration Volume/Volume | Leaflet drop %, day 0 | Leaflet drop %, day 3 | Leaflet drop %, day 7 | Leaflet drop %, day 14 |
|---|---|---|---|---|---|
| Silicone Solution (undiluted with additional water) | 18.5% | Not observed | 12.5% | 20.0% | 22.5% |
| Rubigan[2] | 12 oz/100 gallons | Not observed | 0.0% | 0.0% | 0.0% |

Notes:
[1]No leaflet dropping was observed on initial observation.
[2]Rubigan applied at its highest suggested concentration.

All plots are sprayed 7 and 14 days before the initial evaluation at approximately 100 gallons per acre. The above results were taken 7, 10, 14, and 21 days after the final treatment. 0%=no effect, and 100%=complete effect.

Silicone Solution SLPM01 comprises CAS #063148-62-9, polydimethylsiloxane, a silicone emulsion.

TABLE 6

DETAILED RESULTS FOR SILICONE SOLUTIONS, UNTREATED CONTROL, AND WITH CONTROL (ARMOR ALL ® ) FOR POWDERY MILDEW, FOLIAGE % MILDEW CONTROLLED, AT VARIOUS TIMES

| Treatment | Concentration Volume/ Volume | Mildew Reduction Foliage[1], 4 hrs AT | Mildew Reduction Foliage[1], 1 DA1T | Mildew Reduction Foliage[1], 7 DA1T | Mildew Reduction Foliage[1], 7 DA2T | Mildew Reduction Foliage[1], 14 DA2T |
|---|---|---|---|---|---|---|
| Dow Corning 200 Fluid | 9.25% | 37.5% | 47.5% | 55.0% | 55.0% | 52.5% |
| Dow Corning 244 Fluid | 90.75% | | | | | |
| Dow Corning 200 Fluid | 18.50% | 50.0% | 65.0% | 72.5% | 75.0% | 75.0% |
| Dow Corning 244 Fluid | 81.50% | | | | | |
| Dow Corning 346 Fluid | 15.40% | 60.0% | 70.0% | 63.3% | 70.0% | 66.7% |
| Water | 84.60% | | | | | |
| Dow Corning 346 Fluid | 30.80% | 50.0% | 62.5% | 65.0% | 85.0% | 87.5% |
| Water | 69.20% | | | | | |
| Untreated Control (water) | 100% | 0.0% | 0.0% | 0.0% | 0.0% | 0.0% |
| Armor All ® | 50% | 47.5% | 65.0% | 67.5% | 65.0% | 67.5% |
| Water | 50% | | | | | |

Notes:
[1]Percent powdery mildew reduction per plot.
[2]4 hrs. AT = 4 hours after first treatment
1 DA1T = 1 day after first treatment
7 DA1T = 7 days after first treatment
7 DA2T = 7 days after second treatment
14 DA2T = 14 days after second treatment powdery mildew infection are relatively close to that of the Armor All® solution, and range from 37.5% effective at four hours after the initial treatment with a solution of Dow Corning 200 and Dow Corning 244, to as high as 87.5% (with a mixture of Dow Corning 346 emulsion and water) measured 14 days after a second application.

Turning now to Table 6, this table presents detailed results for silicone solution, untreated control, and with control (Armor All®) for powdery mildew, foliage % mildew controlled. In contrast with Tables 1–5, the data shown in Table 6 indicate the percentages of powdery mildew control (viz. 100%=no mildew, 0%=completely covered with powdery mildew.) As shown, the effectiveness of the various concentrations of the Dow Corning silicone solutions in reducing All plots are sprayed at approximately 50 gallons per acre. 0%=no effect, and 100%=complete effect. The rose variety for all tests was Dr. Huey. Plots were furrow irrigated. Normal cultivation practices were followed. Four replications were conducted for each test.

Turning now to Table 7, this table presents detailed results for silicone solution, untreated control, and with control (Armor All®) for %phytotoxicity. The data shown in Table 7 indicate the percentages of phytotoxicity (yellowing) effect observed (viz. 100%=complete yellowing, 0%=no observable yellowing.) As shown, unlike the GE silicone solution, none of the various concentrations of the Dow Corning silicone solutions or Armor All® solutions caused foliage yellowing.

TABLE 7

DETAILED RESULTS FOR SILICONE SOLUTIONS, UNTREATED CONTROL, AND WITH CONTROL (ARMOR ALL ®) FOR % PHYTOTOXICITY, AT VARIOUS TIMES

| Treatment | Concentration Volume/Volume | Phytotoxicity Foliage, 1 DA1T | Phytotoxicity Foliage, 7 DA1T | Phytotoxicity Foliage, 7 DA2T | Phytotoxicity Foliage, 14 DA2T |
|---|---|---|---|---|---|
| Dow Corning 200 Fluid | 9.25% | 0.0% | 0.0% | 0.0% | 0.0% |
| Dow Corning 244 Fluid | 90.75% | | | | |
| Dow Corning 200 Fluid | 18.50% | 0.0% | 0.0% | 0.6% | 0.0% |
| Dow Corning 244 Fluid | 81.50% | | | | |
| Dow Corning 346 Fluid | 15.40% | 0.0% | 0.0% | 0.0% | 0.0% |
| Water | 84.60% | | | | |
| Dow Corning 346 Fluid | 30.80% | 0.0% | 0.0% | 0.0% | 0.0% |
| Water | 69.20% | | | | |
| Untreated Control (water) | 100% | 0.0% | 0.0% | 0.0% | 0.0% |
| Armor All ® | 50% | 0.0% | 0.0% | 0.0% | 0.0% |
| Water | 50% | | | | |

Notes:
[1]Percent mildew per leaf; five examined leaflets per replicate. Percent of foliage exhibiting symptoms.
[2]1 DA1T = 1 day after first treatment
7 DA1T = 7 days after first treatment
7 DA2T = 7 days after second treatment
14 DA2T = 14 days after second treatment All plots are sprayed at approximately 50 gallons per acre. 0%=no phytotoxicity effect, and 100%=complete phytotoxicity effect. The rose variety for all tests was Dr. Huey. Plots were furrow irrigated. Normal cultivation practices were followed. Four replications were conducted for each test.

Turning now to Table 8, this table presents detailed results for silicone solution, untreated control, and with control (Armor All®) for %leaflet drop. The data shown in Table 8 indicate the percentages of leaflet drop effect observed (viz. 100%=complete loss of leaflets, 0%=no observable leaflet loss) at seven days after the second application. As shown, unlike the GE silicone solution, none of the various concentrations of the Dow Corning silicone solutions or Armor All® solutions caused leaflet dropping.

TABLE 8

DETAILED RESULTS FOR SILICONE SOLUTIONS, UNTREATED CONTROL, AND WITH CONTROL (ARMORALL ®) FOR % LEAFLET LOSS, AT SEVEN DAYS AFTER SECOND APPLICATION

| Treatment | Concentration Volume/Volume | Leaf Loss 7 DA2T |
|---|---|---|
| Dow Corning 200 Fluid | 9.25% | 0.0% |
| Dow Corning 244 Fluid | 90.75% | |
| Dow Corning 200 Fluid | 18.50% | 0.0% |
| Dow Corning 244 Fluid | 81.50% | |

TABLE 8-continued

DETAILED RESULTS FOR SILICONE SOLUTIONS, UNTREATED CONTROL, AND WITH CONTROL (ARMORALL ®) FOR % LEAFLET LOSS, AT SEVEN DAYS AFTER SECOND APPLICATION

| Treatment | Concentration Volume/Volume | Leaf Loss 7 DA2T |
|---|---|---|
| Dow Corning 346 Fluid | 15.40% | 0.0% |
| Water | 84.60% | |
| Dow Corning 346 Fluid | 30.80% | 0.0% |
| Water | 69.20% | |
| Untreated Control (water) | 100% | 0.0% |
| Armor All ® | 50% | 0.0% |
| Water | 50% | |

Notes:
1. Percent mildew per leaf; five examined leaflets per replicate. Percent of foliage exhibiting symptoms.
2. 7 DA2T = 7 days after second treatment All plots are sprayed at approximately 50 gallons per acre. 0%=no effect, and 100%=complete effect. The rose variety for all tests was Dr. Huey. Plots were furrow irrigated. Normal cultivation practices were followed. Four replications were conducted for each test.

As shown and described above, various formulations of silicone solutions are as effective or more effective in controlling fungal infection in plants than presently used antifungal agents. These silicone solutions tested include polydimethylsiloxane and cyclic methylated siloxane compounds. Other forms of siloxanes were not tested, but would likely function similarly. Also, while the silicone compounds were applied by spraying directly onto the surface of the plants (e.g. leaves, leaflets, stems, foliage), the silicone solutions might be taken up systemically and provide prophylaxis and/or reduction of fungi on the plant including powdery mildew infestation.

The drawings and the foregoing description are not intended to represent the only form of the invention in regard to the details of this construction and manner of operation. In fact, it will be evident to one skilled in the art that modifications and variations may be made without departing from the spirit and scope of the invention. Although specific terms have been employed, they are intended in a generic and descriptive sense only and not for the purpose of limitation.

I, claim:

1. A method of reduction of the fungi in plants, consisting essentially of the step of administering a siloxane solution to a plant by spraying the surface of the foliage of the plant with the siloxane solution.

2. The method of reduction of the fungi in plants of claim 1, wherein the plants comprise flowering plants.

3. The method of reduction of the fungi in plants of claim 1, wherein the plants comprise rose plants.

4. The method of reduction of the fungi in plants of claim 1, wherein the siloxane solution consists essentially of methyl siloxane.

5. The method of reduction of the fungi in plants of claim 1, wherein the siloxane solution consists essentially of polydimethyl siloxane.

6. The method of reduction of the fungi in plants of claim 1, wherein the fungi comprises sphaerotheca.

7. A method of reduction of the sphaerotheca in rose plants comprising the step of applying a siloxane solution to the surface of the plant.

8. The method of reduction of the fungi in plants as recited in claim 1 wherein the siloxane solution consists essentially of dimethyl siloxane compounds.

9. A method of reduction of fungi in plants consisting essentially of the step of administering an aqueous solution of siloxane compounds to a plant.

10. A method as recited in claim 9 wherein the siloxane compounds consist essentially of methyl siloxane compounds.

11. A method as recited in claim 9 wherein the siloxane compounds consist essentially of polydimethylsiloxane compounds.

12. A method as recited in claim 9 wherein the siloxane compounds consist essentially of dimethyl polysiloxane compounds.

13. A method as recited in claim 9 wherein the siloxane solution consists essentially of about 18.5% dimethyl polysiloxanes, about 2% of an antimicrobial agent and the balance water-undiluted state.

14. A method as recited in claim 9 wherein the siloxane solution consists essentially of 9.25% dimethylpolysiloxanes, about 1% of an antimicrobial agent and the balance water-undiluted state.

15. A method as recited in claim 9 wherein the siloxane solution is a solution which consists essentially of about 4.625% dimethylpolysiloxanes, about 0.5% of an antimicrobial agent and the balance water-undiluted state.

16. A method of reduction of the fungi in plants consisting essentially of the step of administering siloxane compounds to a plant.

17. A method as recited in claim 16 wherein the siloxane compounds consist essentially of cyclic methylated siloxane compounds.

18. A method as recited in claim 16 wherein the siloxane compounds consist essentially of cyclotetrasiloxane.

19. A method as recited in claim 16 wherein the siloxane compounds consist essentially of octomethylcyclotetrasiloxane.

* * * * *